(12) United States Patent
Fack et al.

(10) Patent No.: US 7,833,516 B2
(45) Date of Patent: *Nov. 16, 2010

(54) COSMETIC COMPOSITION COMPRISING A VOLATILE SILICONE, A SILICONE SURFACTANT AND A CATIONIC SURFACTANT

(75) Inventors: Geraldine Fack, Levallois-Perret (FR); Jonathan Gawtrey, Boulogne-Billancout (FR); Luc Nicolas-Morgantini, Rully (FR); Serge Restle, Saint-Prix (FR)

(73) Assignee: L'Oreal, Paris (FR)

( * ) Notice: Subject to any disclaimer, the term of this patent is extended or adjusted under 35 U.S.C. 154(b) by 1282 days.

This patent is subject to a terminal disclaimer.

(21) Appl. No.: 10/250,362

(22) PCT Filed: Jan. 2, 2002

(86) PCT No.: PCT/FR02/00003

§ 371 (c)(1),
(2), (4) Date: Dec. 5, 2003

(87) PCT Pub. No.: WO02/053112

PCT Pub. Date: Jul. 11, 2002

(65) Prior Publication Data

US 2004/0096416 A1 May 20, 2004

(30) Foreign Application Priority Data

Jan. 2, 2001 (FR) .................................. 01 00015

(51) Int. Cl.
*A61Q 5/12* (2006.01)
*A61Q 5/00* (2006.01)
(52) U.S. Cl. ............... 424/70.19; 424/70.27; 424/70.28
(58) Field of Classification Search .................. None
See application file for complete search history.

(56) References Cited

U.S. PATENT DOCUMENTS 6,602,494 B1 * 8/2003 Jahedshoar et al. ........ 424/70.1
7,476,393 B2 * 1/2009 Dubief et al. ............... 424/401

FOREIGN PATENT DOCUMENTS

| EP | 0 331 833 | 9/1989 |
| EP | 0 576 748 | 1/1994 |
| EP | 0 717 978 | 6/1996 |
| EP | 0 782 846 | 7/1997 |
| WO | WO 99/66883 | 12/1999 |
| WO | WO 01/00141 | 1/2001 |
| WO | WO 01/28506 | 4/2001 |

* cited by examiner

*Primary Examiner*—Jyothsna A Venkat
(74) *Attorney, Agent, or Firm*—Steptoe & Johnson LLP

(57) ABSTRACT

A composition for cosmetic treatment of keratinous materials comprising in a cosmetically acceptable medium, at least a volatile silicone, at least a silicone surfactant and at least a cationic surfactant in a concentration strictly higher than 0.5 wt. % relative to the composition total weight, selected among primary, secondary or tertiary fatty amine salts, optionally polyoxyalkylenated, quaternary ammonium salts and their mixtures. The composition comprises at least an amount of oils containing at least the volatile silicone in a concentration not more than 20 wt.% relative to the composition total weight. A method for cosmetic treatment of keratinous materials is also disclosed.

11 Claims, No Drawings

COSMETIC COMPOSITION COMPRISING A VOLATILE SILICONE, A SILICONE SURFACTANT AND A CATIONIC SURFACTANT

The present invention relates to a composition for cosmetic treatment of keratinous materials, of the water-in-oil emulsion type, comprising in a cosmetically acceptable medium, at least one volatile silicone, at least one silicone surfactant and at least one cationic surfactant, and also relates to a process for cosmetic treatment of keratinous materials.

The mixtures of volatile silicone and silicone surfactant used for hair treatment, and in particular as a hair conditioner, do not produce satisfactory cosmetic properties. Also, after hair is rinsed there are still traces of the mixture on the hair.

The inventors have surprisingly discovered that by introducing a cationic surfactant to a concentration strictly higher than 0.5% by weight, in a mixture of volatile silicone and of silicone surfactant, the hair cosmetic properties are clearly improved, for example, disentangling and softness.

Furthermore, introducing a cationic surfactant into this mixture helps to improve the rinsing capacity of the hair.

The object of the present invention is thus a composition for treating keratinous materials, of the water-in-oil emulsion type, comprising in a cosmetically acceptable medium, at least one volatile silicone, at least one silicone surfactant and at least one cationic surfactant in a concentration strictly higher than 0.5% by weight relative to the total weight of the composition.

Another object of the invention comprises a process for cosmetic treatment of keratinous materials using a composition according to the present invention as described hereinbelow.

Yet another object of the invention is the use of the composition according to the present invention as a hair conditioner.

Other objects, characteristics, aspects and advantages of the invention will emerge even more clearly from the following description and various examples.

According to the present invention the composition for cosmetic treatment of keratinous materials, of the water-in-oil emulsion type, comprises in a cosmetically acceptable medium, at least one volatile silicone, at least one silicone surfactant and at least one cationic surfactant as defined hereinbelow, in a concentration strictly higher than 0.5% by weight relative to the total weight of the composition.

The composition according to the present invention comprises a total quantity of oils comprising at least the volatile silicone, less than or equal to 20% by weight, preferably between 5 and 20% by weight, relative to the total weight of the composition.

"Oil" is understood in the present invention as any fatty compound immiscible with water, which is liquid at ambient temperature.

The oils which can be used in the present invention may further comp rise at least one of the compounds selected from vegetable oils, animal oils, mineral oils, synthetic oils, fatty acid esters, and their mixtures.

Examples of vegetable oil are, in particular, sweet almond oil, avocado oil, castor oil, olive oil, jojoba oil, sunflower oil, wheat germ oil, sesame oil, arachid oil, grape seed oil, soya bean oil, rapeseed oil, safflower oil, copra oil, corn oil, hazelnut oil, karite butter, palm oil, apricot kernel oil, and calophyllum oil.

Perhydrosqualene can especially be cited as animal oil.

Paraffin oil and Vaseline oil can especially be cited as mineral oil.

Examples of synthetic oils are squalane, poly(α-olefins) such as isododecane or isohexadecane, transesterified vegetable oils, fluorinated oils, and their mixtures.

Examples of fatty acid esters are the compounds of formula $R_aCOOR_b$ in which $R_a$ represents a higher fatty acid moiety comprising from 6 to 29 carbon atoms and $R_b$ represents a hydrocarbon chain containing from 3 to 30 carbon atoms, such as Purcellin oil (stearyl octanoate), isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, and 2-octyldodecyl myristate or lactate.

The composition according to the present invention presents in particular a minimum penetration resistance force of 0.075 N, as measured by penetrometry.

The penetrometry measurements were done using a texture TA-TX2 (Rheo) analyser. They correspond to compression force measurements under the following conditions:

(a) displacement of a disc (ébonite cylinder 13 mm in diameter) at a speed of 1 mm/s and detection of the compression resistance force, (b) penetration into the product at the same speed as above to a depth of 10 mm, (c) maintaining compression in the product at this depth for 300 s, and (d) withdrawal of the probe and detection of the breaking force, at a speed of 1 mm/s.

The usable cationic surfactants of the composition according to the present invention are selected from primary, secondary or tertiary fatty amine salts, optionally polyoxyalkylenated, quaternary ammonium salts, and their mixtures.

Particular examples of quaternary ammonium salts are, for example:

(a) those having the following general formula (VI):

in which:

$R_8$ represents a $C_{12-30}$ alkyl, preferably $C_{14-22}$ alkyl, $C_{12-30}$ alkenyl, $(C_{12}$-$C_{22})$ alkylamido$(C_2$-$C_6)$alkyl, $(C_{12}$-$C_{22})$ alkyl acetate group, or an aromatic group such as $C_6$-$C_{12}$ aryl or alkylaryl, $R_9$ to $R_{11}$, which may be identical or different, represent a $C_{1-8}$ alkyl, $C_{1-8}$ alkenyl, $C_{1-8}$ alcoxy, $C_{1-8}$ hydroxyalkyl, $(C_2$-$C_6)$ polyoxyalkylene or $C_{1-8}$ alkylamide group;

X is an anion selected from the group of halides, phosphates, acetates, lactates, $(C_2$-$C_5)$ alkylsulfates, and alkyl- or alkylaryl-sulfonates;

(b) quaternary ammonium salts of imidazoline, such as for example those of the following formula (VII):

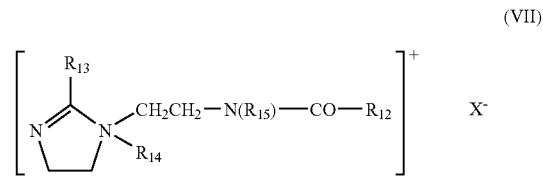

in which $R_{12}$ represents an alkenyl or alkyl radical comprising from 8 to 30 carbon atoms, for example derivatives of tallow fatty acids, $R_{13}$ represents a hydrogen atom, a $C_1$-$C_4$ alkyl radical or an alkenyl or alkyl radical comprising from 8 to 30 carbon atoms, $R_{14}$ represents a $C_1$-$C_4$ alkyl radical, $R_{15}$ represents a hydrogen atom, or a $C_1$-$C_4$ alkyl radical, $X^-$ is an anion selected from the group of halides, phosphates, acetates, lactates, alkyl sulfates, and alkyl- or alkylaryl-sulfonates.

Preferably, $R_{12}$ and $R_{13}$ are a mixture of alkenyl or alkyl radicals comprising from 12 to 21 carbon atoms, for example derivatives of tallow fatty acids, $R_{14}$ is a methyl radical, and $R_{15}$ is a hydrogen atom.

This kind of product is for example marketed as REWO-QUAT® W 75 by REWO;

(c) quaternary diammonium salts of formula (VIII):

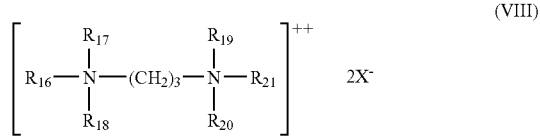

(VIII)

in which $R_{16}$ is an aliphatic radical comprising about 16 to 30 carbon atoms, $R_{17}$, $R_{18}$, $R_{19}$, $R_{20}$ and $R_{21}$, which are identical or different, are selected from hydrogen or an alkyl radical comprising from 1 to 4 carbon atoms, and X is an anion selected from the group of halides, acetates, phosphates, nitrates and methyl sulfates. Such quaternary diammonium salts comprise especially propane-tallow diammonium dichloride;

(d) quaternary ammonium salts containing at least one ester function, such as those of the following formula (IX):

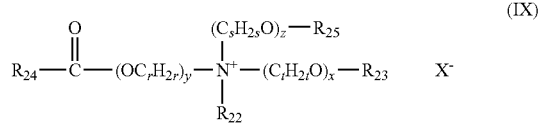

(IX)

in which:

$R_{22}$ is selected from $C_1$-$C_6$ alkyl radicals and $C_1$-$C_6$ hydroxyalkyl or dihydroxyalkyl radicals;

$R_{23}$ is selected from:
(i) the radical

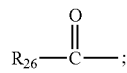

(ii) the linear or branched, saturated or unsaturated. $C_1$-$C_{22}$ hydrocarbon $R_{27}$ radicals; and
(iii) the hydrogen atom.

$R_{25}$ is selected from:
(i) the radical

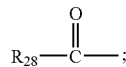

(ii) the linear or branched, saturated or unsaturated $C_1$-$C_6$ hydrocarbon $R_{29}$ radicals; and
(iii) the hydrogen atom, $R_{24}$, $R_{26}$ and $R_{28}$, identical or different, are selected from linear or branched, saturated or unsaturated $C_7$-$C_2$ hydrocarbon radicals;

r, s and t, identical or different, are integers ranging from 2 to 6;

y is an integer ranging from 1 to 10;

x and z, identical or different, are integers ranging from 0 to 10;

$X^-$ is a simple or complex, organic or inorganic anion;

provided that the sum x+y+z is from 1 to 15, when x is 0 then $R_{23}$ is $R_{27}$ and when z is 0 then $R_{25}$ is $R_{29}$.

The alkyl $R_{22}$ radicals may be linear or branched, and more particularly linear.

Preferably, $R_{22}$ is a methyl, ethyl, hydroxyethyl or dihydroxypropyl radical, and more particularly a methyl or ethyl radical.

Advantageously, the sum x+y+z is from 1 to 10.

When $R_{23}$ is a hydrocarbon $R_{27}$ radical, it can be long and have from 12 to 22 carbon atoms, or short and have from 1 to 3 carbon atoms.

When $R_{25}$ is a hydrocarbon $R_{29}$ radical, it preferably has 1 to 3 carbon atoms.

Advantageously, $R_{24}$, $R_{26}$ and $R_{28}$, identical or different, are selected from linear or branched, saturated or unsaturated $C_{11}$-$C_2$, hydrocarbon radicals, and more particularly from linear or branched, saturated or unsaturated $C_{11}$-$C_2$, alkyl and alkenyl radicals.

Preferably, x and z, identical or different, are 0 or 1.

Advantageously, y is equal to 1.

Preferably, r, s and t, identical or different, are 2 or 3, and more particularly still are equal to 2.

The anion is preferably a halide (chloride, bromide or iodide) or an alkylsulfate, more particularly methylsulfate. However, methane sulfonate, phosphate, nitrate, tosylate, an anion derived from organic acid such as acetate or lactate or any other anion compatible with ester-functionnalized ammonium can be used.

The anion $X^-$ is still more particularly chloride or methylsulfate.

Ammonium salts of formula (IX) are more particularly used in the composition according to the present invention, wherein:

$R_{22}$ is a methyl or ethyl radical;
x and y are equal to 1;
z is equal to 0 or 1; and
r, s and t are equal to 2.

$R_{23}$ is selected from:
(i) the radical

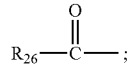

(ii) the methyl, ethyl or $C_{14}$-$C_{22}$ hydrocarbon radicals; and (iii) hydrogen atom.

$R_{25}$ is selected from:
(i) the radical

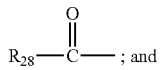

(ii) hydrogen atom, $R_{24}$, $R_{26}$ and $R_{28}$, identical or different, are selected from linear or branched, saturated or unsaturated $C_{13}$-$C_{17}$ hydrocarbon radicals, and preferably from linear or branched, saturated or unsaturated $C_{13}$-$C_{17}$ alkyl and alkenyl radicals.

Advantageously, hydrocarbon radicals are linear.

The following compounds of formula (IX) can be cited, for example, such as diacyloxyethyl dimethyl-ammonium, diacyloxyethyl-hydroxyethyl-methylammonium, monoacyloxyethyl-dihydroxyethyl-methyl ammonium, triacyloxyethyl-methylammonium, monoacyloxyethyl-hydroxyethyl-dimethylammonium salts (chloride or methylsulfate especially) and their mixtures. Acyl radicals preferably have 14 to 18 carbon atoms and originate more particularly from a vegetable oil such as palm oil or sunflower oil. When the compound contains several acyl radicals, these can be identical or different.

These products are obtained, for example, by direct esterification of triethanolamine, triisopropanolamine, alkyldiethanolamine or alkyldiisopropanolamine, optionally oxyalkylenated on fatty acids or on mixtures of fatty acids of vegetable or animal origin, or by transesterification of their methylic esters. This esterification is followed by quaternisation by means of an alkylation agent such as alkyl (methyl or ethyl preferably) halide, dialkyl (methyl or ethyl, preferably) sulfate, methyl methanesulfonate, methyl paratoluenesulfonate, glycol or glycerol chlorhydrine.

Such compounds are for example marketed under the brands DEHYQUART® by HENKEL, STEPANQUAT® by STEPAN, NOXAMIUM® by CECA, and REWOQUAT® WE 18 by REWO-WITCO.

The composition according to the present invention preferably contains a mixture of mono-, di- and triester salts of quaternary ammonium with a majority by weight of diester salts.

A mixture of ammonium salts which can be used, for example, is the mixture containing 15 a 30% by weight of acyloxyethyl-dihydroxyethyl-methylammonium methylsulfate, 45 to 60% of diacyloxyethyl-hydroxyethyl-methylammonium methyl sulfate and 15 to 30% of triacyloxyethylmethylammonium methylsulfate, acyl radicals having from 14 to 18 carbon atoms and originating from palm oil optionally partially hydrogenated.

Ammonium salts containing at least one ester function described U.S. Pat. Nos. 4,874,554 and 4,137,180 can also be used.

Of quaternary ammonium salts of formula (VI), preference is given on the one hand to alkyltrimethylammonium chlorides in which the alkyl radical comprises about 14 to 22 carbon atoms, in particular behenyl trimethyl ammonium, arachidyl trimethyl ammonium, stearyl trimethyl ammonium, cetyl trimethyl ammonium chlorides, or, on the other hand, to palmitylamidopropyl trimethyl ammonium chloride or stearamidopropyldimethyl-(myristyl acetate)-ammonium chloride marketed under the brand CERAPHYL® 70 by VAN DYK.

The especially preferred cationic surfactants in the composition according to the present invention are selected from quaternary ammonium salts, and in particular from behenyl trimethyl ammonium chloride and palmitylamidopropyl trimethyl ammonium chloride.

The composition for cosmetic treatment of keratinous materials preferably comprises the one or more cationic surfactants in a quantity between 0.5 and 10% by weight, better still between 0.8 and 8% by weight, and even more preferably between 1 at 5% by weight relative to the total weight of the composition.

The volatile silicones usable in the invention are linear or cyclic silicones, having a viscosity at ambient temperature and under atmospheric pressure of less than 8 mm$^2$/s (8 cSt).

The viscosity is preferably measured by capillary viscosimetry, for example, by means of a capillary viscosimeter, especially of Ubbelohde type, at a temperature of 25° C., in accordance with the standard ASTM D445-97. The so-called ball drop method can also be used.

Volatile silicones generally have a boiling point between 60° C. and 260° C., and are more particularly selected from:
(i) cyclic volatile silicones comprising from 3 to 7 silicon atoms, and preferably 4 to 5 silicon atoms. This could be, for example, octamethylcyclotetrasiloxane marketed especially under the brand "VOLATILE SILICONE 7207" by UNION CARBIDE or "SILBIONE® 70045 V 2" by RHODIA, decamethylcyclopenta siloxane marketed under the brand "VOLATILE SILICONE 7158" by UNION CARBIDE, "SILBIONE® 70045 V 5" by RHODIA or under the brand DC245 Fluid by DOW CORNING, as well as their mixtures.

Cyclocopolymers of the dimethylsiloxane/methylalkyl siloxane type can also be cited, such as "VOLATILE SILICONE FZ 3109" marketed by UNION CARBIDE, of chemical structure

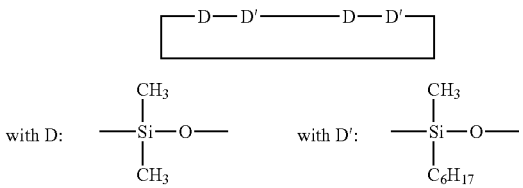

The mixtures of cyclic silicones with organic compounds derived from silicon, such as the mixture of octamethylcyclotetrasiloxane and tetratrimethyl silylpentaerythritol (50/50) and the mixture of octamethylcyclotetrasiloxane and oxy-1,1'-(hexa-2,2,2',2',3,3'-trimethylsilyloxy) bis-neopentane.

(ii) linear volatile silicones having 2 to 9 silicon atoms and having a viscosity less than or equal to 5 mm$^2$/s at 25° C. This can be decamethyltetrasiloxane marketed especially under the brand "SH 200" by TORAY SILICONE. Silicones included in this class are also described in the article of Todd & Beyers, "Volatile silicone fluids for cosmetics", Cosmetics and Toiletries, Vol. 91, Jan. 76, p. 27-32.

The composition according to the present invention preferably comprises volatile silicones in a quantity between 5 and 20% by weight, and more preferably between 8 and 15% by weight relative to the total weight of the composition.

The silicone surfactants usable in the present invention are those well known to the expert. They can be water-soluble, spontaneously water-dispersible or not water-soluble. They are preferably water-soluble or spontaneously water-dispersible.

Silicone surfactants are selected, for example, from compounds of general formulae (I), (II), (III), (IV) and (V)

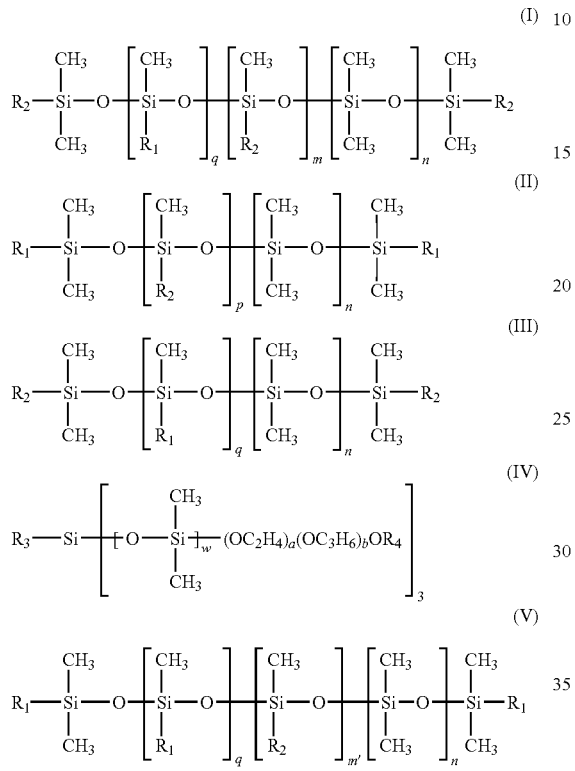

formulae in which:
- $R_1$, identical or different, represents a linear or branched $C_1$-$C_{30}$ alkyl or phenyl group;
- R2, identical or different, represents —$C_cH_{2c}$—O—$(C_2H_4O)_a$—$(C_3H_6O)_b$—$R_5$ or —$C_cH_{2c}$—O—$(C_4H_8O)_a$—$R_5$;
- R3 and $R_4$, identical or different, each is a linear or branched $C_1$-$C_{12}$ alkyl group, and preferably a methyl group;
- R5, identical or different, is selected from hydrogen atom, linear or branched alkyl group comprising from 1 to 12 carbon atoms, linear or branched alcoxy group comprising from 1 to 6 carbon atoms, linear or branched acyl group comprising from 2 to 12 carbon atoms, hydroxyl group, —$SO_3M$, —$OCOR_6$, $C_1$-$C_6$ aminoalcoxy optionally substituted on amine, $C_2$-$C_6$ aminoacyl optionally substituted on amine, —$NHCH_2CH_2COOM$, —$N(CH_2CH_2COOM)_2$, $C_1$-$C_{12}$ aminoalkyl optionally substituted on amine and on the alkyl chain, $C_1$-$C_{30}$ carboxyacyl, a phosphono group optionally substituted by one or two substituted $C_1$-$C_{12}$ aminoalkyl groups, —$CO(CH_2)_dCOOM$, —$OCOCHR_7(CH_2)_dCOOM$, —$NHO(CH_2)_dOH$, or —$NH_3Y$;
- M, identical or different, is a hydrogen atom, Na, K, Li, $NH_4$ or an organic amine;
- R6 is a linear or branched $C_1$-$C_{30}$ alkyl group,
- R7 is a hydrogen atom or a $SO_3M$ group;
- d is from 1 to 10;
- m is from 0 to 20;
- m' is from 1 to 20;
- n is from 0 to 500;
- p is from 1 to 50;
- q is from 0 to 20;
- a is from 0 to 50;
- b is from 0 to 50;
- a+b is greater than or equal to 1;
- c is from 0 to 4;
- w is from 1 to 100; and
- Y represents a monovalent mineral or organic anion such as halide (chloride, bromide), sulfate, or carboxylate (acetate, lactate, citrate).

Preferably, silicone surfactants representing by the general formulae (I) or (II) as defined hereinabove are used, and more particularly, those representing by formulae (I) or (II), in which at least one of, and preferably all, the following conditions are satisfied
- c is equal to 2 or 3;
- $R_1$ is a methyl group;
- $R_5$ represents a hydrogen atom, a methyl group or an acetyl group, and preferably a hydrogen atom;
- a is from 1 to 25, and more particularly from 2 to 25;
- b is from 0 to 25, preferably from 10 to 20;
- n is from 0 to 100; and
- p is from 1 to 20.

The most particularly preferred silicone surfactants are, for example, those sold under the brands FLUID DC 193 and DC 5225C by DOW CORNING, SILWETO L 77 by OSI and MAZIL® 756 by MAZER PPG.

The silicone surfactants are contained in the present invention in a quantity between 0.01 and 3% by weight, better still between 0.2 and 3% by weight relative to the total weight of the composition for treating keratinous materials.

"Cosmetically acceptable medium" is understood to mean a medium compatible with all the keratinous materials such as skin, hair, nails, eyelashes, eyebrows, lips and any other zone of the body and face, but also pleasant odour, appearance and touch.

The cosmetically acceptable aqueous medium comprises water or a mixture of water and a cosmetically acceptable solvent selected from $C_1$-$C_4$ lower alcohols, such as ethanol, isopropanol, tertio-butanol or n-butanol polyols such as propylene glycol; polyol ethers; $C_5$-$C_{10}$ alcanes; $C_{3-4}$ ketones such as acetone and methylethyl ketone; $C_1$-$C_4$ alkyl acetates such as methyl acetate, ethyl acetate and butyl acetate; dimethoxyethane, diethoxyethane; and their mixtures.

The water proportion in the composition according to the present invention is preferably between 30 and 90% by weight relative to the total weight of the composition.

The pH of the inventive compositions is between 4 and 8, preferably between 5 and 7.

The compositions according to the present invention can also contain additives such as cationic, anionic, non-ionic or amphoteric polymers; modified or non-modified non-volatile silicones; associative or non-associative, anionic, amphoteric, zwitterionic, non-ionic or cationic, natural or synthetic, polymeric thickeners; non-polymeric thickeners such as electrolytes; sugars, nacrants, opacifiers, sun filters, perfumes, dyes, organic or mineral particles, preservatives, and pH stabilisers.

A person skilled in the art take care to select the optional additives and the quantity thereof such that they do not harm the properties of the compositions of the present invention.

These additives are present in the composition according to the present invention in a quantity ranging from 0 to 50% by weight relative to the total weight of the composition.

The inventive compositions can be in the form of fluid or thickened liquids, gels, creams, or simple or multiple emulsions.

The compositions can be used, for example, as shampoos, colouring or bleaching products or perm products, hair-styling products, rinse treatments, deep-cleansing masks, shower gels, lotions or creams for treating the scalp, shaving products or depilation products.

The present invention also relates to a process for cosmetic treatment of keratinous materials, consisting of applying an effective quantity of a composition as described hereinabove, on keratinous materials, and optional rinsing after optional rest time.

According to a preferred embodiment of the invention, the composition can be used as a hair conditioner.

The following examples illustrate the present invention but should not in any way be considered as limiting the invention.

EXAMPLES

Hair conditioner compositions were prepared from the ingredients indicated in the table below. The indicated contents are expressed in % by weight relative to the total weight of the composition.

|  | Ex. 1 | Ex. 2 | Ex. 3 | Ex. 4 |
|---|---|---|---|---|
| Cyclopentadimethylsiloxane [1] | 8.1 | 7 | 5.4 | 10.1 |
| Isopropyl myristate | — | — | 2.1 | — |
| Polyamino siloxane | — | — | — | 2 |
| Polydimethyl/methyl(396/4)siloxane (18 moles of ethylene oxide/18 moles of propylene oxide) [2]-DC 5225C by DOW CORNING | 0.9 AM | 0.5 AM | 0.5 AM | 0.5 AM |
| Palmitylamidopropyl trimethyl ammonium chloride | — | 1.2 | 2.7 | 1.2 |
| Behenyltrimethyl ammonium chloride | 3.2 | — | — | — |
| Propylene glycol | — | 0.8 | 7.3 | 2.5 |
| Saccharose | — | — | 29.5 | — |
| Glycerin | — | 40.8 | — | — |
| Benzotriazole filter derived from heptamethyl hydrogenotrisiloxane | — | — | — | 1 |
| Water | 100 | 100 | 100 | 100 |

AM: active materials
[1] DC 245 by DOW CORNING
[2] at 10% in cyclopentadimethylsiloxane The compositions were applied to the hair which was rinsed after a rest period of one minute, with rinsing being easy. The hair was then dried.

The dried hair is soft and flowing to the touch and has no unpleasant residue.

The invention claimed is:

1. A composition for cosmetic treatment of keratinous materials, in the form of a water-in-oil emulsion, comprising, in a cosmetically acceptable medium, at least one volatile silicone, at least one silicone surfactant wherein the silicone surfactant is present in a quantity between 0.01 and 3% by weight relative to the total weight of the composition and at least one cationic surfactant in a concentration wherein the cationic surfactant is present in a quantity between 0.5 and 10% by weight relative to the total weight of the composition, wherein the at least one volatile silicone is a cyclic volatile silicone comprising 3 to 7 silicon atoms, wherein the volatile silicone is present in a quantity between 5 and 20% by weight relative to the total weight of the composition;

wherein the cationic surfactant is a quaternary ammonium salt, the quaternary ammonium salt being:

a salt having the following general formula (VI):

in which:

$R_8$ represents a $(C_{12}-C_{22})$ alkylamido$(C_2-C_6)$alkyl, $(C_{12}-C_{22})$ alkyl acetate group, $R_9$ to $R_{11}$, which may be identical or different, represent a $C_{1-8}$ alkyl, $C_{1-8}$ alkenyl, $C_{1-8}$ alkoxy, $C_{1-8}$ hydroxyalkyl, $(C_2-C_6)$ polyoxyalkylene or $C_{1-8}$ alkylamide group;

X is an anion which is a halide, phosphate, acetate, lactate, $(C_2-C_6)$ alkylsulfate, or alkyl- or alkylarylsulfonate;

wherein the at least the silicone surfactant is a compound of formula (II),

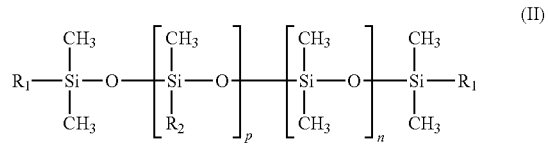

in which:

a) $R_1$, identical or different, represents a linear or branched $C_1-C_{30}$ alkyl or phenyl group;

b) $R_2$, identical or different, represents —$C_cH_{2c}$—O—$(C_2H_4O)_a$—$(C_3H_6O)_b R_5$ or —$C_cH_{2c}$—O—$(C_4H_a$—$R_5$;

c) $R_5$, identical or different, is a hydrogen atom, a linear or branched alkyl group comprising from 1 to 12 carbon atoms, a linear or branched alkoxy group comprising from 1 to 6 carbon)atoms, a linear or branched acyl group comprising from 2 to 12 carbon atoms, a hydroxyl group, —$SO_3M$—$OCOR_6$, $C_1-C_6$ aminoalkoxy, optionally substituted on the amine, $C_2-C_6$ aminoacyl, optionally substituted on the amine, —$HCH_2CH_2COOM$, —$N(CH_2CH_2COOM)_2$, $C_1-C_{12}$ aminoalkyl, optionally substituted on the amine and on the alkyl chain, $C_1-C_{30}$ carboxyacyl, a phosphono group, optionally substituted by one or two substituted $C_1-C_{12}$ aminoalkyl groups, —$CO(CH_2)_dCOOM$, —$COCHR_7(CH_2)_dCOOM$, or —$NHO(CH_2)_dOH$, —$NH_3Y$;

d) M, identical or different, is a hydrogen atom, Na, K, Li, $NH_4$ or an organic amine;

e) $R_6$ is a linear or branched $C_1-C_{30}$ alkyl group;

f) $R_7$ is a hydrogen atom or a $SO_3M$ group;

g) d is from 1 to 10;

h) n is from 0 to 500;

i) p is from 1 to 50;

j) a is from 0 to 50;

k) b is from 0 to 50;

l) a+b is greater than or equal to 1;

m) c is from 0 to 4; and n) Y represents a monovalent mineral or organic anion.

2. The composition for cosmetic treatment of keratinous materials as claimed in Claim 1, wherein the cationic surfactant is present in a quantity between 0.8 and 8% by weight relative to the total weight of the composition.

3. The composition for cosmetic treatment of keratinous materials as claimed in claim 2, wherein the cationic surfactant is present in a quantity between 1 and 5% by weight relative to the total weight of the composition.

4. The composition for cosmetic treatment of keratinous materials as claimed in Claim 1, wherein the volatile silicone is present in a quantity between 8 and 15% by weight relative to the total weight of the composition.

5. The composition for cosmetic treatment of keratinous materials as claimed in Claim 1, wherein the silicone surfactant is a compound of formula (II) in which at least one of the following conditions are satisfied:
  a) c is equal to 2 or 3;
  b) $R_1$ is a methyl group;
  c) $R_5$ represents a hydrogen atom, a methyl group or an acetyl group;
  d) a is from 1 to 25;
  e) b is from 0 to 25;
  f) n is from 0 to 100; and
  g) p is from 1 to 20.

6. The composition for cosmetic treatment of keratinous materials as claimed in Claim 1, wherein the silicone surfactant is present in a quantity between 0.2 and 3% by weight relative to the total weight of the composition.

7. The composition for cosmetic treatment of keratinous materials as claimed in claim 1, wherein the cosmetically acceptable medium is water or a mixture of water and a cosmetically acceptable solvent.

8. The composition for cosmetic treatment of keratinous materials as claimed in claim 7, wherein the cosmetically acceptable solvent is a $C_1$-$C_4$ lower alcohol, polyol, polyol ether, $C_5$-$C_{10}$ alkane, $C_{3-4}$ ketone, $C_1$-$C_4$ alkyl acetate, dimethoxyethane, diethoxyethane, or mixtures thereof.

9. The composition for cosmetic treatment of keratinous materials claimed in claim 1, further comprising an additive which is a cationic, anionic, non-ionic or amphoteric polymer; modified or unmodified non-volatile silicone; associative or non-associative, anionic, amphoteric, zwitterionic, non-ionic or cationic, natural or synthetic polymeric thickener; non-polymeric thickener; sugar, nacrant, opacifier, sun filter, perfume, dye, organic or mineral particle, preservative, or pH stabiliser.

10. A process for cosmetic treatment of keratinous materials, comprising applying a composition for cosmetic treatment of keratinous materials as claimed in claim 1 to the keratinous materials.

11. The process for cosmetic treatment of keratinous material as claimed in claim 10, wherein the composition is a hair conditioner.

* * * * *